United States Patent [19]

Machak et al.

[11] Patent Number: 4,733,973

[45] Date of Patent: Mar. 29, 1988

[54] METHOD AND APPARATUS FOR TESTING GLASSWARE

[75] Inventors: David R. Machak; Ronald A. Puvak; Russell D. Southwick, all of Butler, Pa.

[73] Assignee: American Glass Research, Inc., Butler, Pa.

[21] Appl. No.: 862,113

[22] Filed: May 12, 1986

[51] Int. Cl.$^4$ ............................................. G01M 25/72
[52] U.S. Cl. .......................................... 374/5; 73/49.3; 141/94; 374/57
[58] Field of Search ...................... 374/4, 57, 5; 73/8, 73/864.66, 864.61; 141/7, 94

[56] References Cited

U.S. PATENT DOCUMENTS

| | | | |
|---|---|---|---|
| 2,167,185 | 7/1939 | Preston | 374/5 |
| 3,365,930 | 1/1968 | Arias | 374/57 |
| 3,805,593 | 4/1974 | Sandoz et al. | 73/49.2 |
| 3,911,972 | 10/1975 | Hubers et al. | 141/7 |
| 4,109,508 | 8/1978 | Fukuyama | 374/5 |
| 4,291,573 | 9/1981 | Richter et al. | 73/49.2 X |
| 4,575,257 | 3/1986 | Ogura et al. | 374/57 |

FOREIGN PATENT DOCUMENTS 0180838  12/1984  U.S.S.R. ............................... 73/49.2

Primary Examiner—Daniel M. Yasich
Attorney, Agent, or Firm—Buchanan Ingersoll

[57] ABSTRACT

A glass container to be tested for resistance to thermal schock and impact simulation is first filled with hot water to a point of overflowing. The hot water fill is terminated and the excess permitted to run off. Thereafter the bottle is closed and the external surface is sprayed with cold water to induce a thermal stress upon the container. After the cold water spray a low level internal pressure load is applied to the container following the thermal shock load. The application of the internal pressure extends partial fractures resulting in complete breakage of the container or a break resulting in a decrease of pressure in the container, indicating a failure.

20 Claims, 1 Drawing Figure

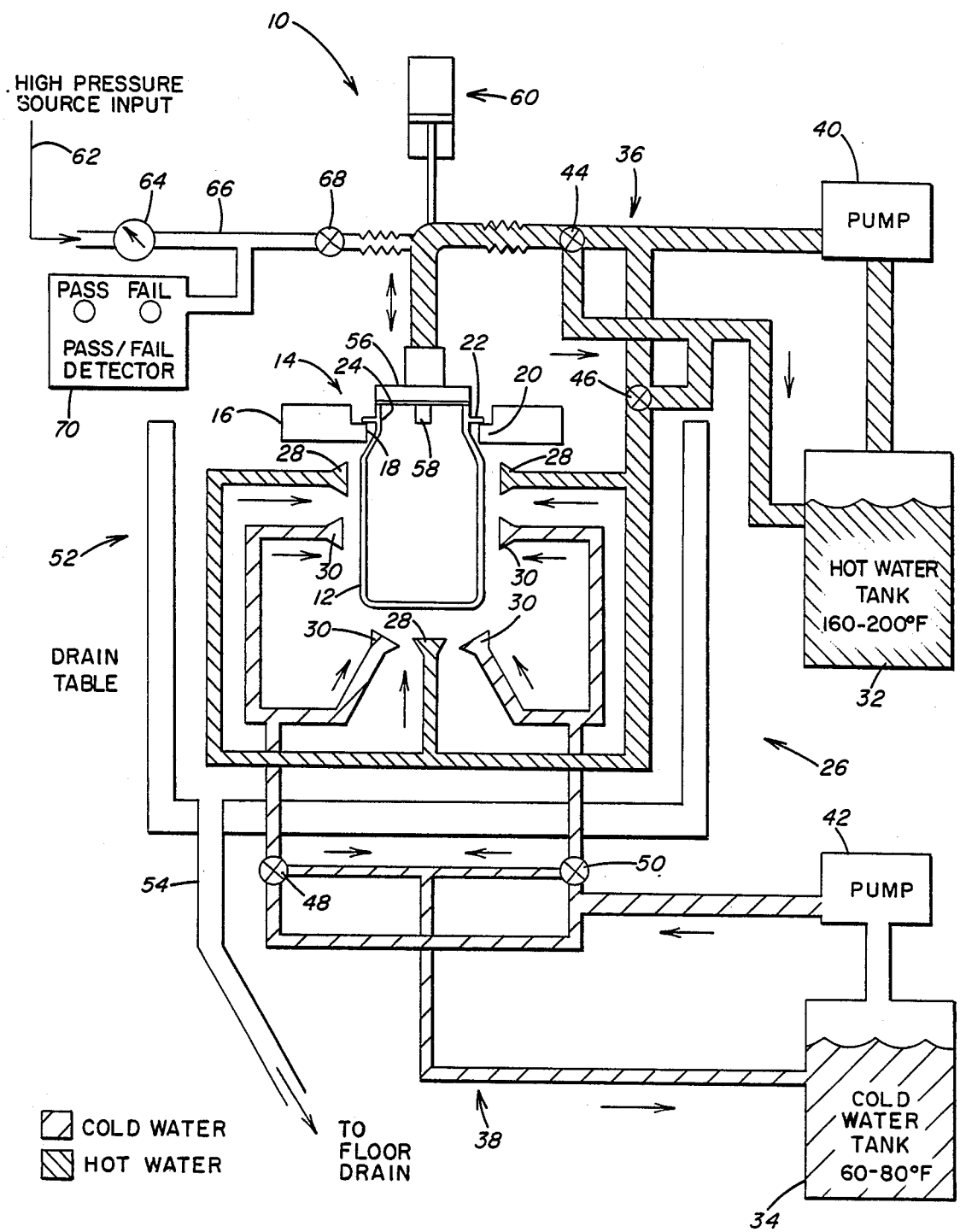

METHOD AND APPARATUS FOR TESTING GLASSWARE

BACKGROUND OF THE INVENTION

1. Field of the Invention

This invention relates to apparatus for testing glassware for defects and more particularly to a method and apparatus for testing the resistance of glassware to thermal shock and impact loads.

2. Description of the Prior Art

Commercial glassware and specifically glass bottles are tested to prevent ware of inferior quality from leaving the factory and for the purpose of effecting any changes in the glass or in production. During the bottling, handling the packaging stages glassware is subjected to both thermal and impact stresses. For example, in the pasteurizing process bottles are subjected to a long-enduring temperature gradient which may be rather low. Then on other occasions a severe temperature gradient may be encountered. A beverage bottle, for example, taken from a warm room and placed in an ice chest or a tank of ice water is subjected for a period of time to a severe temperature gradient. A mason jar which is initially at a little above room temperature may be poured full of boiling fruit juices. Bottles are subjected to a variety of impact loads such as when labels are forcibly applied to flat panels of a bottle and when bottles are case packed. Consequently, glass bottles must adhere to certain minimum requirement insofar as resistance to thermal and impact loads.

The containers which do not meet the minimum requirements must be detected during the manufacturing process prior to filling and handling the bottle. It is the conventional practice to test the thermal endurance of glassware by either setting up tension in the outside wall of the ware or setting up compression in the inside wall. It is well known to cause tension in the outer walls of glassware by dipping a hot bottle into a cold liquid and by pouring a hot liquid into a cold bottle. When hot liquid is poured into a cold bottle the tension that is applied is indirect. The hot liquid in contact with the inside of the article sets up compression in the inner walls thereby placing the outer walls in tension.

A well known thermal tester is disclosed in U.S. Pat. No. 2,167,185 whereby a bottle is subjected to hot and cold baths to induce fracture at defective points in the bottle. A basket is loaded with bottles and immersed in a tank of hot water to a point where the bottles are completely filled with water. The bottles remain in the tank of hot water for approximately five minutes. Thereafter the basket is transferred to a cold water tank where it remains for thirty seconds. The bottles are immersed in the cold tank to a point below the top of the bottle. The basket is removed from the cold water tank, and the individual bottles are visually inspected to detect any breakage.

U.S. Pat. No. 2,764,015 discloses a device for detecting a defect in a glass container by controlled differential heating. The interior surface of the container is rapidly heated in about one second to create a momentarily high tensile strength in the outer exterior surface. The rapid heating of the interior surface without corresponding heating of the exterior surface results in the creation of temporary stresses which will break the container at the point or points of location of the external surface defects. The interior surface of the container is quickly heated by hot gasses, such as steam or compressed air, to a high temperature with the result that the exterior surface is subjected to high tensile stress causing breakage if a defect should exists.

Another well known method for testing glassware for both thermal and mechanical weaknesses is disclosed in U.S. Pat. No. 2,301,316 where articles to be tested are conveyed through a fluid bath heated to a desired temperature. The fluid bath is maintained at a temperature of 500° F. so as to subject the articles to thermal shock of sufficient magnitude to destroy the articles which are unfit for use.

While thermal endurance tests can reveal defects in different parts of a container, such as flaws in the bottom parting line, lower sidewall, or baffle, impact tests are applied at only one point. Thus only limited information on the impact endurance of a bottle can be obtained. Commonly known methods for testing impact resistance are dropping weights on the object, using a heavy pendulum, or squeezing the bottle. Because of the different sizes and shapes of bottles these tests do not provide consistent information unless the tests are carefully applied at the same part of the bottle.

The known method of thermal shock testing by submerging bottles in one tank and then transferring them to a second tank of a different temperature is a time-consuming task that interrupts the production process. The test must be manually performed and if the test is successful in producing a fracture the fracture must be detected upon visual inspection. If the visual inspection is not conducted diligently, then the flaw will go undetected.

A container may remain intact as a result of a thermal shock test in which a partial fracture has occurred. The container will have been substantially weakened, but the flaw will not be visibly detected. As a result there will be no advance warning of an upcoming problem.

Overall the realiability of both the known impact and thermal shock test methods are dependent on the diligence of an operator to visually examine the test sample to determine if breakage has occurred. Therefore there is need for a method and apparatus for detecting substandard resistance of glassware to impact and determining thermal shock.

The known methods are time consuming and labor intensive. Separate tests have to be conducted for determining shock and impact endurance. In many cases the glassware to be tested is removed from a production line and tested while production continues. Consequently if flaws are detected the line must be shut down and all products retrieved even though they may have continued onto subsequent stages. Therefore there is need for a method and apparatus for testing thermal and impact endurance of glassware in an automated fashion to the extent that sample bottles are selected, tested and examined for breakage without operator assistance.

SUMMARY OF THE INVENTION

In accordance with the present invention there is provided glassware testing apparatus that includes a test station. Holder means stationarily supports a glassware container at the test station. A fluid reservoir is provided. A plurality of nozzles are positioned in a selected array at the test station around the container to direct a spray of fluid over substantially the entire surface of the container. Conduit means connects the nozzles with the reservoir for conveying fluid under pressure from the reservoir to the nozzles. A means is connected to the conduit means for heating a portion of the fluid to an elevated temperature. Control means directs the heated portion of the fluid through the conduit means into the container to fill the container to an overflow condition. The control means is operable to direct fluid at a lower temperature from the reservoir to selected nozzles for spraying fluid upon the container outer surface following heating thereof by the overflow of heated fluid out of the container.

Further in accordance with the present invention there is provided glassware impact simulation apparatus that includes a test station. Holder means stationarily supports a glassware container at the test station. Fluid means first fills the container to an overflow condition with a fluid heated to an elevated temperature and second sprays the exterior surface of the container with fluid at a temperature less than the elevated temperature to apply a thermal stress on the container. A source of pressurized fluid is conveyed by conduit means to the container after applying the thermal stress upon the container. Means is provided for sealing the container to prevent escape of the pressurized fluid and maintain an internal pressure load on the container.

Further in accordance with the present invention there is provided a method for testing the thermal resistance of a glass container that comprises the steps of filling a container with a fluid at a preselected temperature. The container is maintained filled with the fluid at the preselected temperature for a preselected time interval. Thereafter the exterior surface of the container is sprayed with fluid maintained at a preselected temperature differential with respect to the temperature of the fluid in the container to subject the container to a thermal shock stress.

Additionally in accordance with the present invention there is provided a method for detecting breakage of a glass container that comprises the steps of subjecting a glass container to a thermal gradient within a selected time interval to apply a thermal shock load on the container. The container is internally pressurized to apply an internal pressure upon the container. A fracture due to the thermal shock load is advanced in the container by the internal pressure load. The fracture initiated by the thermal shock load is detected.

Further in accordance with the present invention there is provided a method for sensing a fracture of a glass container due to thermal shock stress comprising the steps of subjecting a glass container to a thermal shock load. The interior of the container is sealed. The sealed container is internally pressurized to advance fractures in the container originating from the thermal shock load. The internal pressure of the container is sensed to detect a loss of internal pressure. A fracture in the container is identified by a reduction in the internal pressure of the container.

Accordingly, the principal object of the present invention is to provide a method and apparatus for testing glass containers to identify structural defects in the manufacture of the containers.

Another object of the present invention is to provide apparatus for use on an automated glassware sampling line for detecting minimum resistance to thermal shock in a glass container.

Another object of the present invention is to provide method and apparatus for detecting in a glass container a partial fracture condition originated as a result of a thermal shock load and not detectable by visual inspection.

An additional object of the present invention is to provide an automated method for testing and examining glassware subjected to thermal and simulated impact endurance tests.

Another object of the present invention is to provide a method and apparatus for detecting a number of types of defects in glassware that would result in low level internal pressure breakage or heel hinge impact breakage.

Another object of the present invention is to provide thermal shock testing apparatus that utilizes internal pressure loading to detect breakage due to the application of a thermal shock load.

A further object of the present invention is to provide a tester to detect in glassware defects which can lead to low level impact and vertical load breakage.

These and other objects of the present invention will be more completely and described in the following specification, the accompanying drawings and the appended claims.

BRIEF DESCRIPTION OF THE DRAWINGS

The FIGURE is a schematic illustration of apparatus for conducting thermal and impact simulation tests on glassware.

DESCRIPTION OF THE PREFERRED EMBODIMENT

Referring to the FIGURE there is illustrated apparatus 10 for detecting defects in glassware and principally a glass bottle or container 12 which is stationarily positioned at a test station generally designated by the numeral 14. The test station 14 includes a bottle holder 16 having an opening 18 of a preselected diameter for receiving the container 12. Surrounding the opening 18 is a shoulder 20 of the holder 16. Preferably the shoulder 20 receives the upper threads or transfer ring 22 of the container 12 to hold it in place for testing. The container 12 has an open end portion 24 positioned above the ring 22. With this arrangement the container 12 is securely held in a stationary position for testing.

The container 12 is connected to a fluid recirculation system generally designated by the numeral 26. The recirculation system 26 is connected to an array of nozzles that are divided into two sets of nozzles generally designated by the numerals 28 and 30. The array of nozzles 28 and 30 are positioned at the test station 14 around the container 12 so as to effectively direct a concentrated spray of fluid over the substantially the entire exterior surface of the container 12.

The fluid recirculation system 26 provides for the flow of a selected fluid from a fluid reservoir that includes a first tank 32 associated with the nozzles 28 and a second tank 34 associated with the nozzles 30. In the embodiment of the present invention shown in the FIGURE, the first tank 32 contains water as the fluid which is heated to a preselected temperature, preferably in the temperature range of 160°-200° F. above ground water temperature. The second tank 34 contains water at a ground temperature, for example 60°-80° F. The tanks 32 and 34 are insulated.

The tank 32 is connected to the plurality of nozzles 28 by a conduit system generally designated by the numeral 36. The cold water tank 34 is connected to the nozzles 30 by a conduit system generally designated by the numeral 38. Thus nozzles 28 constitute the hot nozzles, and nozzles 30 constitute the cold nozzles.

A pump 40 is positioned in the conduit system 36 to draw hot water from the tank 32 and deliver it through the system 36 to the nozzles 28. A pump 42 draws water from the cold water tank 34 and supplies it through the conduit system 38 to the cold water nozzles 30. Flow of hot water from the tank 32 through the pump 40 to the hot nozzles 28 is controlled by a pair of valves 44 and 46. When the valves 44 and 46 are opened, hot water is supplied to the nozzles 28. When the valves 44 and 46 are closed, hot water in the conduit system 36 is constantly circulating through the tank 32 to maintain the water at a preselected constant, elevated temperature.

Valves 48 and 50 in the cold water conduit system 38 control the flow of cold water to the cold nozzles 30. When the valves 48 and 50 are closed, the cold water is circulated through the system 38 back to the cold water tank 34. Thus, with the recirculation system 26 the desired fluid temperatures in the conduit systems 36 and 38 to the nozzles 28 and 30 are maintained to establish a selected temperature in a range between 100°–120° F., i.e. the hot water is maintained at a temperature of 100°–120° F. above the cold water temperature which is maintained at a temperature between 60°–80° F.

The valving system permits fluid to be directed either to the sets of nozzles or back to the respective tanks for recirculation. This overcomes the problem of fluid in the system 26 losing the desired temperature differential where the cold water increases in temperature and the hot water decreases in temperature between tests. Such a change in temperature would preclude the application of the desired thermal shock load, thereby reducing the accuracy and reproducibility of the tests.

A drain table generally designated by the numeral 52 catches the overflow and drain water from the hot fill and spray from the nozzles 28 and water from the cold spray from the nozzles 30. A floor drain 54 removes the collected water from the drain table 52.

The open end 24 of container 12 is closed by the provision of a seal 56 movable between open and closed positions by operation of a seal control mechanism 60, such as piston cylinder assembly. Associated with the seal 56 is a fill tube 58 that extends through the seal 56 and communicates with the conduit system 36 associated with the hot water tank 32. The container 12 is filled with the seal 56 in the open position to permit overflow of the container 12. The container 12 is closed by lowering the seal 56 on opening 24 after the overflow and an interval of stand time during which hot water flows over the exterior surface of the container 12. Once the seal 56 is lowered, the cold spray of the exterior surface of the container 12 is initiated.

Actuation of the control mechanism 60 opens the seal 56 to permit fluid to enter and overflow the container 12 through the tube 58. The container 12 is filled with hot water from the tank 32, once the valves 44 and 46 have been opened. Simultaneously with the entry of hot water into the container 12, hot water is sprayed from the nozzles 28 onto the exterior surface of the container 12.

Preferably the fill and spray time for the hot water ranges between 5–16 seconds. In one example the hot water flow rate is 5.9 gal./min. (13 fl. oz./sec.). The bottle 12 is filled until it overflows permitting excess hot water to flow downwardly onto the exterior surface of the container while a continuous spray of hot water is directed from the nozzles 28 onto the exterior surface of the container 12. Preferably a minimum hot fill time of 5 seconds is needed for a 16 fluid ounce container.

After the hot fill of the container 12, the flow from the tank to the container 12 is interrupted. During this stand time excess water is permitted to drain off the container 12 into the drain table 32. A stand time of preferably between 3 to 5 seconds is permitted between the termination of the hot fill and the initiation of the cold spray. During the stand time the control mechanism 60 is activated to seal the interior of the container 12.

After the stand time the cold spray is initiated and continues for 3–5 seconds. During this period of time the container 12 is subjected to a thermal shock load. The container 12 is then internally pressurized at the end of the cold spray for a duration of about 3 seconds with a pressure in the range 20–50 psi.

After the cold spray, the container 12 is internally pressurized by flow of fluid from a high pressure source 62 through a pressure regulator valve 64, conduit 66, valve 68, and the fill tube 58 into the interior of the container 12. The conduit 66 communicates with the fill tube 58 through which hot water is introduced into the container 12. The pressure regulator 64 reduces the pressurized fluid to the desired pressure level which preferably is in the range of 20–50 psi. The pressurized fluid may be either a gas or liquid.

Generating an internal pressure load in the container 12 permits detection of a fracture resulting from the application of the thermal shock load. The valve 68 is operable to permit the flow of the pressurized gas or liquid to enter the container through the tube 58 only at the desired time at the end of the cold spray.

By subjecting the container 12 to an internal pressure load following the application of the thermal shock load, detection of any fracture, full or partial, from the thermal shock load is automatically recorded by a pass-/fail detector 70. The detector 70 communicates with the conduit 66 through which the pressurized fluid flows to the container 12. Therefore, the detector is capable of sensing any pressure loss which would occur in the pressure line that extends into the container 12.

In the event of a fracture, even one not readily visible, the pressure in the container 12 and the conduit 66 will drop activating the detector 70 to indicate by actuation of an alarm that the tested container has failed the thermal shock test. Thus, the application of the internal pressure load within the container 12 is an effective means by which to detect a fracture resulting from the cold spray.

By utilizing the internal pressure load, it is possible with the present invention to detect defective baffles in a container resulting in low level heel hinge impact breakage. This type of test is not efficiently reproducible with conventional processes of detecting infolding in the baffle by impact tests. The conventional impact test is capable only of detecting infolding in the baffle in the large sidewall locations. The present invention will detect infolding in the baffle in locations other than in the side wall locations.

With the present testing procedure utilizing the internal pressure loading, the problems of partial fractures going undetected is avoided. In the event a partial fracture would not extend to a full fracture under the action of internal pressure load, a loss of internal pressure is nevertheless recorded by the detector 70. Therefore visual inspections are obviated, permitting automation of the detection process after the test process on an automated sampling line. Consequently, operator discrimination errors are not encountered.

Not only is the present invention applicable for detecting resistance to thermal shock load, it has application in the detection of defects which may lead to low level impact loads. This permits the apparatus 10 to be utilized in more than one testing capacity, particularly when it is desired to test certain containers which do not encounter thermal shock loads but do encounter impact loads. An example of a glass container that does not encounter thermal shock loads but does encounter low level impact loads is a flat-paneled salad dressing bottle. This type of bottle is subjected to heel hinge-type impact breakage during filling and does not normally encounter thermal stresses during the filling or during the manufacture.

It has been found that by testing a flat-paneled salad dressing bottle by the thermal shock test of the present invention the test for detecting a heel hinge-type impact breakage is duplicated. A salad dressing bottle was both conventionally impact tested and tested in accordance with the present invention and it was found that those bottles which experienced heel hinge-type breakage during filling failed the thermal shock test of the present invention. This was the case where a temperature gradient of 105° F. was maintained and found to be the equivalent to an impact test level of 1.8 in. lbs.

The following table is a summary of a test for detecting defective baffles capable of resulting in low level heel hinge impact breakage in 8 ounce salad dressing bottles. The bottles were thermal shock tested in accordance with the present invention and conventionally impact tested. The bottles were impacted on the flat sidewall panel at a height of about 2½ in. above the bearing surface at a level of 35 inches per second. The thermal shock and impact testing was performed on comparable bottle samples. The thermal shock tests with the present invention did not produce any breakages on bottles determined to be acceptable by conventional thermal shock and impact test. In all cases, the thermal shock tests with the present invention detected breakages on glass mold cavities having defective ware as determined by conventional thermal shock and impact tests. The column entitled "Test Parameters" describes the specific test situation. For example, 105° T/40 psi/5 seconds refers to a 105° F. temperature differential, a 40 pounds per square inch internal pressure load, and a 5 second delay between the start of the cold spray and the start of the internal pressure load.

The three columns entitled "Test Results" explain the outcome of a specific test. If the test sample failed the thermal shock and pressure tests, it was referred to as a Complete Failure. Fail TS/Pass Pressure describes those bottles in which a fracture resulted from the thermal shock load, but the container remained intact following the internal pressure load. The partial fracture condition was eliminated by the time delay of more than three seconds between the start of the cold spray and the start of the internal pressure load.

Summary of In-Plant Testing
8 ounce Salad Dressing Bottle

| Bottles Tested | | | Test Results | | |
|---|---|---|---|---|---|
| Number | Cavity | Test Parameters | Complete Failure | Fail T.S./ Pass Press. | No Break |
| 5 | 27 | 105° T/50 psi/3 sec | 5 | 0 | 0 |
| 5 | 5 | 105° T/50 psi/3 sec | 4 | 1 | 0 |
| 18 | mixed | 105° T/20 psi/5 sec | 7 | 0 | 11 |
| 18 | mixed | 90° T/20 psi/5 sec | 0 | 0 | 18 |
| 36 | mixed | 84° T/20 psi/5 sec | 0 | 0 | 36 |
| 36 | mixed | 100° T/20 psi/5 sec | 0 | 0 | 36 |
| 18 | mixed | 105° T/20 psi/5 sec | 1 | 0 | 17 |
| 5 | 24 | 105° T/20 psi/5 sec | 5 | 0 | 0 |
| 10 | 2 | 95° T/20 psi/5 sec | 1 | 0 | 9 |
| 10 | 2 | 105° T/20 psi/5 sec | 4 | 0 | 6 |
| 18 | mixed | 100° T/20 psi/5 sec | 1 | 0 | 17 |
| 5 | 19 | 100° T/20 psi/5 sec | 3 | 0 | 2 |
| 5 | 19 | 100° T/20 psi/3 sec | 4 | 1 | 0 |
| 5 | 8 | 100° T/20 psi/5 sec | 3 | 0 | 2 |

Thus with the present invention a more rapid and reliable thermal shock test can be performed in comparison with the standard thermal shock test. In addition specific types of defects, typically not associated with thermal shock breakage, can now be detected. Using an internal pressure load following the completion of the cold spray application provides breakage detection method. The present invention thus facilitates the automation of selecting, testing and examining bottles for breakage without operator assistance. The tester has application for association with cavity identification equipment and use as an on-line sampling test device.

According to the provisions of the patent statutes, we have explained the principle, preferred construction and mode of operation of our invention and have illustrated and described what we now consider to represent its best embodiments. However, it should be understood that, within the scope of the appended claims, the invention may be practiced otherwise as specifically illustrated and described.

We claim:

1. Glassware testing apparatus for producing a thermal shock stress on glassware comprising,
   a test station,
   holder means for stationarily supporting a glassware container at said test stand,
   a fluid reservoir,
   a plurality of nozzles positioned in a selected array at said test station around the container,
   conduit means connecting said nozzles with said reservoir for conveying fluid under pressure from said reservoir to said nozzles to direct a spray of fluid from said nozzles over substantially the entire surface of the container,
   temperature differential means for heating a first portion of the fluid in said reservoir to an elevated temperature above a second portion of the fluid in said reservoir,
   first control means for directing a flow of the first portion of the fluid through said conduit means into the container to fill the container with heated fluid to an overflow condition to rapidly increase the temperature of the glassware,
   second control means for directing the second portion of the fluid at a lower temperature than the first portion of the fluid from said reservoir to selected nozzles for spraying fluid upon the container outer surface following heating thereof by the overflow of heated fluid out of the container, and said first control means interrupting the flow of fluid at an elevated temperature to the container prior to actuation of said second control means for directing fluid at a lower temperature upon the container to induce a thermal shock stress on the container.

2. Glassware testing apparatus as set forth in claim 1 which includes,
means for recirculating the fluid between said nozzles and said temperature differential means for heating the first portion of the fluid to maintain the first portion of the fluid at a preselected temperature over the second portion of the fluid.

3. Glassware testing apparatus as set forth in claim 1 which includes,
seal means for closing the interior of the container after filling the container with water as a fluid,
a source of fluid under pressure, and
means for conveying pressurized fluid into the container to exert an internal pressure load after filling the container with water.

4. Glassware testing apparatus as set forth in claim 1 in which,
said conduit means includes a first tank and conduit system for supplying water at an elevated temperature above ground water temperature to a first set of nozzles,
a second tank and conduit system for supplying water at ground water temperature to a second set of said nozzles, and
said first and second control means controlling the flow of water between said first and second tanks and said first and second sets of nozzles respectively.

5. Glassware impact simulation apparatus comprising,
a test station,
holder means for stationarily supporting a glassware container at said test station,
fluid means for first filling the container to an overflow condition with a fluid heated to an elevated temperature, interrupting the flow of heated fluid, and thereafter spraying the exterior surface of the container with fluid at a temperature less than the elevated temperature to induce a thermal stress on the container,
a source of fluid under pressure,
conduit means for conveying the fluid under pressure to the container after inducing the thermal stress upon the container, and
means for sealing the container to prevent escape of the fluid to maintain an internal pressure load on the container to detect breakage of the container as a result of the induced thermal stress.

6. Glassware impact simulation apparatus as set forth in claim 5 which includes,
means for sealing the container to maintain a preselected pressure within said container, and
an actuator for opening and closing the container between the first position for filling the container with water heated to an elevated temperature and the second position for sealing the container to pressurize the container.

7. Glassware impact simulation apparatus as set forth in claim 5 which includes,
a pressure regulator for controlling the pressure within the container.

8. Glassware impact simulation apparatus as set forth in claim 5 which includes,
means for detecting a loss of pressure within the container after the container has been internally pressurized to a preselected magnitude.

9. A method of testing the thermal resistance of a glass container comprising the steps of,
filling a container with a fluid at a preselected elevated temperature,
maintaining the container filled with the fluid at the preselected elevated temperature for a preselected time interval,
interrupting the flow of fluid at the preselected elevated temperature to the container, and
thereafter spraying the exterior surface of the container with a fluid maintained at a preselected temperature differential below the temperature of the fluid in the container to induce a thermal shock stress on the container.

10. A method is set forth in claim 9 which includes,
simultaneously filling the container and spraying the exterior of the container with water heated to an elevated temperature,
overflowing the heated water onto the exterior of the container,
letting the container stand to permit the overflow of heated water to run off the exterior of the container, and
spraying the exterior of the container with cold water with a temperature in the range between 100°-120° F. below the elevated temperature of the water.

11. A method as set forth in claim 9 which includes,
filling the container with fluid heated to an elevated temperature and spraying the exterior of the container for a time interval between 5-16 seconds, with the heated fluid.

12. A method as set forth in claim 9 which includes,
terminating fill of the container after a preselected time interval,
letting the container stand prior to external spraying,
spraying the exterior of the container for a time interval between 3-5 seconds with fluid maintained at a temperature between 100°-120° F. below the temperature of the external spray.

13. A method as set forth in claim 9 which includes,
externally spraying the container with cold water maintained at a ground water temperature, and
applying an internal pressure within the container following the cold water external spray.

14. A method for detecting breakage of a glass container comprising the steps of,
subjecting a glass container to a thermal gradient within a selected time interval by rapidly filling the container with fluid at an elevated temperature and immediately thereafter spraying the container with fluid at a substantially lower temperature to apply a thermal shock load on the container,
interrupting spraying the container,
internally pressurizing the container to apply an internal pressure load upon the container to advance a fracture due to the applied thermal shock load, and
thereafter detecting a breakage of the container initiated by the thermal shock load.

15. A method is set forth in claim 14 which includes,
filling the container with hot water,
thereafter spraying the container with cold water maintained at a temperature between 100°-120° F. below the temperature of the hot water to induce a thermal shock on the container, and pressurizing the container to detect breakage of the container as a result of the thermal shock applied to the container.

16. A method as set forth in claim 14 which includes, applying upon the container an internal pressure between 20–50 lb. per sq. in. for an interval of three seconds.

17. A method as set forth in claim 14 which includes, simultaneously filling the container to an overflow condition and spraying the exterior of the container for an interval between 5–16 seconds with hot water maintained at a temperature between 100°–120° F. above ground water temperature, and prior to pressurizing the container, spraying the container with water at ground temperature for an interval of 3–5 seconds to induce thermal stress upon the container.

18. A method for sensing a fracture of a glass container due to thermal shock stress comprising the steps of, sealing the interior of the container,
subjecting a glass container to a thermal shock load by first filling the glass container with a fluid at an elevated temperature and thereafter spraying the external surface of the glass container with fluid maintained at a preselected temperature differential below the temperature of the fluid in the container,
internally pressurizing the sealed container to advance fractures in the container originating from the thermal shock load,
sensing the internal pressure of the container to detect a loss of internal pressure, and
identifying a fracture in the container by a reduction in the internal pressure of the container.

19. A method as set forth in claim 18 which includes, pressurizing the interior of the container after termination of an external spray upon the container to induce an internal pressure load on the container to detect a fracture in the container resulting from the thermal shock load subjected to the container.

20. A method as set forth in claim 18 which includes, measuring the internal pressure of the container after pressurizing the container to determine a loss in pressure due to breakage of the container.

* * * * *

UNITED STATES PATENT AND TRADEMARK OFFICE
CERTIFICATE OF CORRECTION

PATENT NO. : 4,733,973

DATED : March 29, 1988

INVENTOR(S) : David R. Machak, et al.

It is certified that error appears in the above-identified patent and that said Letters Patent is hereby corrected as shown below:

In the Abstract, line 2, delete "schock" and insert -shock-;

Col 1, line 16, after handling delete 'the' and insert -and-;

Col 6, line 35, at the end of the line delete "pass-" and insert -pass-.

Signed and Sealed this

Twenty-third Day of August, 1988

Attest:

DONALD J. QUIGG

*Attesting Officer*　　*Commissioner of Patents and Trademarks*